United States Patent
von Borstel et al.

(10) Patent No.: US 10,125,385 B2
(45) Date of Patent: Nov. 13, 2018

(54) ELECTROCHEMILUMINESCENCE (ECL) DETECTION REAGENTS AND RELATED METHODS FOR MEASURING ENZYME ACTIVITY

(71) Applicant: Wellstat Diagnostics, LLC, Gaithersburg, MD (US)

(72) Inventors: Reid W. von Borstel, Potomac, MD (US); Paul Q. Hu, Frederick, MD (US); Lana Hoang Do, Chantilly, VA (US); Xiaofen Huang, Gaithersburg, MD (US)

(73) Assignee: PDL BIOPHARMA, INC., Incline Village, NV (US)

( * ) Notice: Subject to any disclaimer, the term of this patent is extended or adjusted under 35 U.S.C. 154(b) by 0 days.

(21) Appl. No.: 14/770,115

(22) PCT Filed: Feb. 25, 2014

(86) PCT No.: PCT/US2014/018425
§ 371 (c)(1),
(2) Date: Aug. 25, 2015

(87) PCT Pub. No.: WO2014/131046
PCT Pub. Date: Aug. 28, 2014

(65) Prior Publication Data
US 2016/0002695 A1 Jan. 7, 2016

Related U.S. Application Data

(60) Provisional application No. 61/769,044, filed on Feb. 25, 2013, provisional application No. 61/840,820, filed on Jun. 28, 2013.

(51) Int. Cl.
| | | |
|---|---|---|
| *C07C 333/16* | (2006.01) | |
| *C12Q 1/00* | (2006.01) | |
| *C12Q 1/44* | (2006.01) | |
| *C12Q 1/32* | (2006.01) | |
| *G01N 21/76* | (2006.01) | |

(52) U.S. Cl.
CPC ............... *C12Q 1/008* (2013.01); *C12Q 1/32* (2013.01); *C12Q 1/44* (2013.01); *G01N 21/76* (2013.01); *G01N 2333/904* (2013.01); *G01N 2333/92* (2013.01); *G01N 2458/40* (2013.01)

(58) Field of Classification Search
CPC ... C12Q 1/08; C12Q 1/32; C12Q 1/44; G01N 21/76; G01N 2333/09; G01N 2458/40
USPC .......................................................... 556/38
See application file for complete search history.

(56) References Cited

U.S. PATENT DOCUMENTS

| | | | | |
|---|---|---|---|---|
| 5,057,302 A | * | 10/1991 | Johnson ................ | C07C 275/42 424/1.17 |
| 2003/0054396 A1 | * | 3/2003 | Weiner ................... | B82Y 30/00 435/6.12 |
| 2004/0248325 A1 | * | 12/2004 | Bukusoglu ......... | G01N 33/5088 436/548 |
| 2005/0112685 A1 | | 5/2005 | Amiss et al. | |
| 2012/0157332 A1 | * | 6/2012 | Kumar ............. | G01N 33/54386 506/9 |

OTHER PUBLICATIONS

The extended European search report, dated Sep. 13, 2016, for European Applciation No. 14754657.6, which is a co-pending application to U.S. Appl. No. 14/770,115.
Anonymous, "ab133091—PAF Acetylhydrolase Inhibitor Screening Assay Kit", Jan. 1, 2012, pp. 1-16, retrieved from the Internet: URL:http:www.abcam.com/ps/products/133/ab133091 PAF Acetylhydrolase Inhibitor Screening Assay Kit-protocol (website). pdf; retrieved on Aug. 23, 2016.
Jameison et al., "Electrochemiluminescence-Based Quantitation of Classical Clinical Chemistry Analytes," Analytical Chemistry, vol. 68, No. 8, Jan. 1, 1996, pp. 1298-1302.
Yang et al., "Rapid and sensitive immunomagnetic-electrochemiluminescent detection of p53 antibodies in human serum," J Immunological Methods, vol. 288, No. 1-2, May 1, 2004, pp. 47-54.
Slim et al., "DNA-Protein Noncovalent Cross-Linking: Ruthenium Dipyridophenazine Biotin Complex for the Assembly of Proteins and Gold Nanoparticles on DNA Templates," ChemBioChem, vol. 8, No. 7, May 7, 2007, pp. 804-812.
Slim et al., "Ruthenium (II)-Phenanthroline-Biotin Complexes: Synthesis and Luminescence Enhancement upon Binding to Avidin," Bioconjugate Chemistry, vol. 15, No. 5, Sep. 1, 2004, pp. 949-953.
International Search Report for International Application No. PCT/US14/18425, dated Jul. 18, 2014, and Written Opinion for International Application No. PCT/US14/18425, dated Jul. 18, 2014.

\* cited by examiner

*Primary Examiner* — Clinton Brooks
*Assistant Examiner* — Kofi Adzamli (57) ABSTRACT

Disclosed are methods of measuring enzyme activity in a sample. The methods use disulfide-containing detection reagents with an electrochemiluminescent functional group.

26 Claims, 4 Drawing Sheets

(Compound 1)

FIG. 1A (Compound 2)

FIG. 2

ELECTROCHEMILUMINESCENCE (ECL) DETECTION REAGENTS AND RELATED METHODS FOR MEASURING ENZYME ACTIVITY

This is a national stage application of International Application No. PCT/US2014/018425, filed internationally on Feb. 25, 2014, which claims priority to U.S. Provisional Patent Application Nos. 61/769,044, filed Feb. 25, 2013, and 61/840,820, filed Jun. 28, 2013, each of which is herein incorporated by reference in its entirety.

FIELD

The present disclosure relates generally to the development of detection reagents and electrochemiluminescence (ECL)-based assays, and reagent test kits for the detection and the quantitative measurement of enzymes in a biological sample. In particular, the present disclosure relates to methods of detecting and measuring enzyme activity in a sample using disulfide-containing detection reagents with an electrochemiluminescent functional group.

BACKGROUND

The measurement of enzyme activity in blood or plasma can be a useful detector and predictor of developing disease conditions and risk factors. Assays for blood and plasma enzyme activity that can be performed in a clinical setting may be used to rapidly determine which patients would receive, for example, an inhibitor in the case of pathological enzyme over-activity, or they may be used as diagnostic indices of tissue damage, disease pathology, or to detect the presence of toxic enzyme inhibitors.

Standard clinical chemical assays exist for measuring clinically-relevant enzyme activity or the presence of enzyme inhibitors. Some of these assays can measure the targeted enzyme activity by changing the amounts of NADPH (reduced form of nicotinamide adenine dinucleotide phosphate) or NADH (reduced form of nicotinamide adenine dinucleotide) in a reaction mixture, whether directly or by additional reaction-mixture enzymes and substrates which couple the measurement of activity of a targeted enzyme to a change in NADH or NADPH. Currently, these assays use a color-change or other known detection methods to obtain their quantitative detection readouts. However, there is a need for detection reagents and methods that enable electrochemiluminescence (ECL) measurements of clinical chemistry enzyme activities, which can be used by coupling the cleavage of its disulfide bond to, for example, changes in NADPH, NADH, or a free sulfhydryl group, to provide the desired quantitative detection readout of enzyme activity.

SUMMARY

The disclosure relates generally to a detection reagent, comprising a molecule having a cleavable disulfide bond with an electrochemiluminescence (ECL)-active ruthenium chelate on a first side of the disulfide bond and an immobilizing moiety on a second side of the disulfide bond.

In some embodiments, the disclosure relates to a detection reagent, wherein the disulfide bond of the detection reagent is capable of being cleaved by a free sulfhydryl group.

The disclosure relates generally to methods of preparing a detection reagent, comprising attaching to a molecule having a cleavable disulfide bond, an electrochemiluminescence (ECL)-active ruthenium chelate on a first side of the disulfide bond and an immobilizing moiety on a second side of the disulfide bond.

The disclosure relates generally to methods of preparing a detection reagent, comprising forming a cleavable disulfide bond between a first molecule and a second molecule; attaching an electrochemiluminescent functional group to the first molecule; and attaching an immobilizing moiety to the second molecule.

In some embodiments, the disclosure relates to methods of preparing a detection reagent, wherein the disulfide bond of the detection reagent is capable of being cleaved by a free sulfhydryl group.

The disclosure relates generally to methods for measuring NADPH generated in a sample, comprising combining a detection reagent having a disulfide bond, the sample and an NADPH-catalyzed disulfide reductase to form a reaction mixture, wherein the disulfide bond of the detection reagent is cleaved by the reductase in the presence of NADPH, wherein the detection reagent contains an ECL-active ruthenium chelate on a first side of the disulfide bond and an immobilizing moiety on a second side of the disulfide bond, wherein the cleaving yields a first cleavage product having the ECL-active ruthenium chelate and a second cleavage product having the immobilizing moiety, and wherein the cleaving by the reductase is in proportion to the amount of NADPH generated in the sample; and measuring the absence, presence or amplitude of an ECL signal, wherein the absence or reduced magnitude of an ECL signal indicates the presence of NADPH in the sample, and wherein a maximal ECL signal indicates the absence of NADPH in the sample.

In some embodiments, the disclosure relates generally to methods for measuring NADPH generated in a sample, wherein the NADPH-generating enzyme is glucose-6-phosphate dehydrogenase.

In some embodiments, the disclosure relates generally to methods for measuring NADPH generated in a sample, wherein the disulfide-cleaving reductase is chosen from glutathione reductase and trypanothione reductase.

The disclosure relates generally to methods for measuring an NADPH-generating enzyme activity in a sample comprising (a) combining the sample, NADP+, and a substrate specific to the enzyme to be measured within the sample, to form a reaction mixture, under conditions such that NADPH is generated; (b) combining the reaction mixture of step (a) with glutathione reductase and glutathione disulfide under conditions that will reduce glutathione disulfide to reduced glutathione; (c) combining the reaction mixture of step (b) with a disulfide-containing detection reagent having an ECL-active ruthenium chelate on a first side of the disulfide bond and an immobilizing moiety on a second side of the disulfide bond, wherein the disulfide-containing detection reagent is cleaved nonenzymatically by the reduced glutathione, wherein the cleaving by the reduced glutathione is in proportion to the amount of NADPH generated in the sample; and (d) measuring the absence, presence or amplitude of an ECL signal, wherein the absence or reduced magnitude of an ECL signal indicates the presence of NADPH-generating enzyme in the sample, and wherein a maximal ECL signal indicates the absence of NADPH-generating enzyme in the sample.

In some embodiments, the disclosure relates generally to methods for measuring an NADPH-generating enzyme activity in a sample, wherein step (a) is carried out over a specified time and at a specified temperature appropriate for the particular reaction.

In some embodiments, the disclosure relates generally to methods for measuring an NADPH-generating enzyme activity in a sample, wherein the disulfide-cleaving reductase is chosen from glutathione reductase and trypanothione reductase.

In some embodiments, the disclosure generally relates to methods for measuring an NADPH-generating enzyme in a sample, wherein the NADPH-generating enzyme is glucose-6-phosphate dehydrogenase.

The disclosure relates generally to methods for measuring esterase activity in a sample, comprising combining a reaction mixture, including the sample having an esterase, a thioester analog of a substrate for an esterase, and a disulfide-containing detection reagent having an ECL-active ruthenium chelate on a first side of the disulfide bond and an immobilizing moiety on a second side of the disulfide bond, under conditions such that the thioester analog of the substrate is deacylated by esterase in the reaction mixture to yield an activated substrate analog having an exposed deacylated free sulfhydryl group which cleaves the disulfide bond of the disulfide-containing detection reagent leading to a change in a detectable ECL signal in proportion to the esterase activity in the reaction mixture; and measuring the ECL signal.

In some embodiments, the disclosure relates generally to methods for measuring esterase activity in a sample, wherein the esterase is Lp-PLA$_2$ (platelet activating factor acetylhydrolase).

In some embodiments, the disclosure relates generally to methods for measuring esterase activity in a sample, wherein the thioester analog of a substrate is chosen from thio-platelet activating factor (PAF), lyso-thio-PAF, acetylthiocholine, propionylthiocholine and butyrylthiocholine.

In some embodiments, the disclosure relates generally to methods for measuring esterase activity in a sample, wherein the immobilizing moiety is biotin.

In some embodiments, the disclosure relates generally to methods for measuring esterase activity in a sample, the combining step further comprising combining a detergent.

In some embodiments, the disclosure relates generally to methods for measuring esterase activity in a sample, wherein the detergent is chosen from CHAPS (cholamidopropyl)dimethylammonio]-1-propanesulfonate) and Triton™ X-100 (4-(1,1,3,3-Tetramethylbutyl)phenyl-polyethylene glycol, t-Octylphenoxypolyethoxyethanol, Polyethylene glycol tert-octylphenyl ether).

In some embodiments, the disclosure relates generally to methods for measuring esterase activity in a sample, further comprising the step of adjusting the pH after the combining step and before the measuring step.

The disclosure relates generally to kits for performing the methods described herein. In some embodiments, the kit may include a disulfide-containing detection reagent; a thioester analog of a substrate for an esterase; and instructions for performing an esterase activity measuring assay comprising the steps of combining a reaction mixture, comprising the sample having an esterase, a thioester analog of a substrate for an esterase, and a disulfide-containing detection reagent having an ECL-active ruthenium chelate on a first side of the disulfide bond and an immobilizing moiety on a second side of the disulfide bond, under conditions such that the thioester analog of the substrate is deacylated by esterase in the reaction mixture to yield an activated substrate analog having an exposed deacylated free sulfhydryl group which cleaves the disulfide bond of the disulfide-containing detection reagent leading to a change in a detectable ECL signal in proportion to the esterase activity in the reaction mixture; and measuring the ECL signal.

BRIEF DESCRIPTION OF THE DRAWINGS

The accompanying table and figures are incorporated in, and constitute a part of this specification.

DETAILED DESCRIPTION

Detection Reagent

The present disclosure provides a detection reagent useful in assays and methods for detecting and measuring enzyme activity. The detection reagent permits the measuring of enzyme activity on standard electrochemiluminescence (ECL)-based assays, and may be useful in assay panels and for use on a point of care instrument. The detection reagent may be a molecule or compound having a cleavable disulfide bond or a dithio chemical group of —S—S—. In some embodiments, the detection reagent may have at least one electrochemiluminescent functional group, such as an electrochemiluminescence (ECL)-active ruthenium chelate, on a first side of the disulfide bond. In some embodiments, the detection reagent may have an immobilizing moiety on a second side of the disulfide bond.

In some embodiments, the disulfide bond of the detection reagent is capable of being cleaved by a free sulfhydryl group that has been exposed by the reaction of components in a reaction mixture. The components in the reaction mixture may include at least one unknown analyte, such as an enzyme, a substrate, or a metabolite, the detection reagent, buffers and assay reagents, and a biological sample, such as blood, plasma, serum, red blood cell lysate, saliva, urine, and tissue extracts. Upon mixing of the components of the reaction mixture, conditions may be created, in some embodiments, which allow the enzyme to act, independently or in conjunction with other components in the reaction mixture, and ultimately expose a free sulfhydryl group. The free sulfhydryl group may then cleave the disulfide bond of the detection reagent having the electrochemiluminescent functional group. In some embodiments, the detection reagent is capable of being cleaved in proportion to the amount of the enzyme present in the sample and/or the reaction mixture.

The electrochemiluminescent functional group may serve as a detection label or tag that may be detected or quantified within an ECL reaction chamber, such as in a flow cell, or on a disposable electrode. The immobilizing moiety may serve to hold the detection reagent near an ECL electrode in the ECL reaction chamber during detection. Thus, for example, when the disulfide bond of the detection reagent is cleaved, the electrochemiluminescent functional group may be detached from the immobilizing moiety, and therefore go undetected as it may be washed away in an assay washing step. This then may reduce the ECL signal generated by the application of voltage to the ECL-activating electrode in an ECL reaction chamber. Both the electrochemiluminescent functional group and the immobilizing moiety may be directly attached to the disulfide bond or indirectly attached via linking intermediates that may be used to connect the electrochemiluminescent functional group or immobilizing moiety to the disulfide bond. Suitable immobilizing moieties may be various solid phase mediums including, but not limited to, plates, wells, disposable ECL electrodes, biotin, and paramagnetic or magnetic beads that may be coated with avidin or streptavidin or have other surface functionalities to promote binding affinity. Suitable linking intermediates may include biotin, carboxylate or amino groups, or other chemical bonds.

In some embodiments, the detection reagent may be prepared by attaching to a molecule or a compound having a disulfide bond, at least one electrochemiluminescent functional group, such as an electrochemiluminescence (ECL)-active ruthenium chelate, to a first side of the disulfide bond and an immobilizing moiety to a second side of the disulfide bond. Linking intermediates described herein may also be used to indirectly connect the electrochemiluminescent functional groups and the immobilizing moieties to the disulfide bond.

In some embodiments, other molecular scaffolds may be used to form the detection reagent. Any suitable molecular moieties with a sulfide group capable of forming a disulfide bond and that are capable of attaching to either an electrochemiluminescent functional group or an immobilizing moiety may be used to form the detection reagent. For example, glutathione disulfide, as discussed herein, may provide a suitable molecular scaffold for a detection reagent as it has a disulfide bond and the glutathione moieties are capable of attaching to the electrochemiluminescent functional group and the immobilizing moiety to form a detection reagent.

Thus, in some embodiments, the detection reagent may be prepared by attaching an electrochemiluminescent functional group to a first molecule having a sulfide group capable of forming a disulfide bond; attaching an immobilizing moiety to a second molecule having a sulfide group capable of forming a disulfide bond; and forming a disulfide bond between the first molecule and the second molecule.

In some embodiments, the detection reagent may be prepared by forming a disulfide bond between a first portion of a first molecule and a first portion of a second molecule; attaching an electrochemiluminescent functional group to a second portion of the first molecule; and attaching an immobilizing moiety to a second portion of the second molecule. It is contemplated that these steps do not have to be completed in the order provided herein, and may be performed in different orders, where, for example, the immobilizing moiety is attached first to a molecule and then the disulfide bond is formed between the first and second molecules. It is further contemplated that the electrochemiluminescent functional group and immobilizing moiety may be attached to either the first or the second molecules and in varying order. The disulfide bond of the detection reagent is capable of being cleaved by a free sulfhydryl group.

Electrochemiluminescence (ECL) is the process whereby a molecular species, such as an "ECL label", luminesces upon the exposure of that species to electrochemical energy in an appropriate surrounding chemical environment. ECL is a rapid and sensitive bio-analytical detection technique that is a regenerative process. Some of the advantages achieved with ECL as a detection method in biological sample analysis include simpler, less expensive instrumentation; stable, nonhazardous labels; and increased assay performance characteristics such as lower detection limits, higher signal to noise ratios, and lower background levels. Certain applications of ECL have been developed and reported in the literature. U.S. Pat. Nos. 5,147,806, 5,068,808, 5,061,445, 5,296,191, 5,247,243, 5,221,605, 5,238,808, 5,310,687, 5,714,089, 6,165,729, 6,316,607, 6,808,939, 6,881,589, 6,881,536, and 7,553,448, the disclosures of which are incorporated herein by reference, detail certain methods, apparatuses, chemical moieties, inventions, and associated advantages of ECL.

Electrochemiluminescence signals are generated by a redox reaction between an electrochemiluminescent functional group, such as an ECL-active label with a redox substrate that occurs at the surface of an electrode. In certain embodiments, the ECL label is a ruthenium(Ru)-containing reagent. One example of a suitable electrochemiluminescent label is Tris(bypyridine)ruthenium(II) ($[Ru(bipy)3]^{2+}$, also referred to as TAG). In some embodiments, the redox substrate is tripropylamine (TPA).

In some embodiments, a magnet usually positioned below an electrode may attract the magnetic beads, pulling down the Ru-labeled complex near the electrode. The Ru may then be oxidized. Oxidized tripropylamine (TPA) may react with the oxidized Ru, which then may emit a photon. The redox reaction between Ru and the redox substrate tripropylamine (TPA) that occurs only in the electric field near the electrode may be a regenerative process during continued application of voltage, which allows for an ECL signal that undergoes amplification over time. Because photons can only be generated near the electrode surface, electrochemiluminescence only occurs when the Ru is brought into proximity with the electrode by the magnet, thereby reducing background levels. Nonspecific ECL is not triggered by any known natural constituents of biological samples; therefore, unlike chemiluminescence, which often displays background artifacts due to nonspecific triggering of chemiluminescent detector molecules, ECL maintains reduced background levels.

Enzyme Activity Methods and Assays

The detection reagent disclosed herein may be used in various formats of assays and methods that measure, quantify, and/or detect enzyme activity. A wide array of enzymes may be used with the detection reagent, including, but not limited to, glutathione reductases, trypanothione reductases, NADPH-generating enzymes, NADPH-depleting enzymes, NADH-generating enzymes, NADH-depleting enzymes, liver transaminases, lipases, esterases, glycosyltransferases, esterifying enzymes, kinases, synthetases and ATPases. Furthermore, substrates for such enzymes can be measured with similar enzyme reaction mixtures in which the presence of the specific substrate leads to the generation or utilization of NADPH or NADH, or results in production of free sulfhydryl groups.

In some embodiments, disulfide-containing detection reagent disclosed herein, may be cleaved by a free sulfhydryl group generated in a reaction mixture with the intended target enzyme, in proportion to the amount of the intended target enzyme activity present in a biological sample. The free sulfhydryl groups produced in the reaction mixture, in proportion to the activity of the enzyme of interest or amount of the substrate of interest, equilibrate with the disulfide bond of the detection reagent, cleaving said bond in proportion to the amount of free sulfhydryl groups produced in the reaction mixture. A similar principle underlies the known uses of 5,5'-dithiobis-(2-nitrobenzoic acid) (DTNB; Ellman's reagent), which undergoes a quantifiable color change in response to alterations in free sulfhydryl group amounts in a reaction mixture. The detection reagent disclosed herein uniquely enables an alternative method of detection for measurement of a wide variety of enzyme activities by electrochemiluminescence.

NADPH-Generating Enzymes

The disulfide-containing detection reagent disclosed herein may be used in various methods, including methods for measuring NADPH generated in a sample, methods for measuring NADPH-generating enzyme activity in a sample, methods for measuring NADPH-depleting enzyme activity in a sample and methods for measuring glucose-6-phosphate dehydrogenase (G6PD) activity in a sample.

In some embodiments, the disulfide bond-containing detection reagent disclosed herein may be used in assays that measure glucose-6-phosphate dehydrogenase (G6PD) activity in a biological sample. The reaction of glucose-6-phosphate with G6PD uses NADP+ as a cofactor, which is converted to NADPH. Genetic deficiency of G6PD is relatively common, affecting about 400 million people worldwide, and can result in serious toxicities, such as hemolysis, in response to some therapeutic drugs, including antimalarial agents, and after exposure to agents in some foods, such as fava beans, which can cause hemolysis in people with G6PD deficiency. Thus, assays that measure G6PD activity may be useful for determining whether someone with malaria should receive, for example, primaquine or tafenoquine versus another antimalarial drug, which may be less effective against a particular strain of malaria, but will not trigger a toxic reaction related to G6PD deficiency.

Typically, in most G6PD activity assays, NADPH generated by reaction of glucose-6-phosphate in the presence of NADP+ with G6PD is quantified by the color of a redox-sensitive substrate such as a tetrazolium salt. More generally, a common format in clinical chemistry analyzers uses reaction mixtures for measuring enzyme activities by coupling them to changes in the amount of NADH or NADPH, either by reaction with a redox-sensitive color reagent or simply by the difference in UV absorbance between NAD+ or NADP+ and their corresponding reduced forms, NADH or NADPH, respectively.

In the methods of the present disclosure, the amounts of NADH or NADPH in a reaction mixture can be translated into quantitative alterations in the amount of free sulfhydryl groups, produced in proportion to the amount of NADH or NADPH generated, which is in turn proportional to the activity of the enzyme to be quantified. For example, by adding an NADH- or NADPH-dependent reductase, such as glutathione reductase or cystine reductase along with their respective substrates, glutathione disulfide or cysteine, to a reaction mixture, and combining those enzymes with the components in the reaction mixture that either generate or deplete NADPH or NADH, disulfide bonds may be formed or broken, and ultimately measured or used to measure enzyme activity based on the interaction with the detection reagent disclosed herein. The assay reaction is run for a specific time and at a specific temperature sufficient to provide an adequate dynamic range for determination of either enzyme activities (which are generally expressed in units encompassing as amounts of product produced per time) or unknown amounts of substrates in biological samples.

In some embodiments, glucose-6-phosphate dehydrogenase (G6PD) activity in a biological sample may be coupled to an ECL assay when NADPH, generated by G6PD reacted with glucose-6-phosphate present in the biological sample in the reaction mixture, is used to cleave a disulfide bond of the reagent component of the reaction mixture. For such an assay, glutathione disulfide (GSSG; oxidized glutathione; a glutathione dimer with a disulfide bridge), used in combination with the enzyme glutathione reductase, may be suitable for quantifying enzymes generating or using up NADPH. Glutathione monomers (GSH; reduced glutathione) with free sulfhydryl groups cleave the disulfide bond in the ECL detection reagent disclosed herein; thus, altering the amplitude of the ECL signal in proportion to the amount of NADPH present or generated in the reaction mixture.

For ECL-based assays, using glutathione disulfide, it is also possible to link NADPH generation by G6PD (or other enzymes that generate NADPH) directly to the alteration of an ECL signal without intermediary production of sulfhydryl groups in the reaction mixture. In one embodiment, a detection reagent comprising an ECL-functional group linked to a first glutathione moiety of GSSG (or a GSSG analog), and an immobilizing moiety linked to a second glutathione (or glutathione moiety), is cleaved directly by an NADPH-dependent reductase capable of catalyzing such cleavage. For example, trypanothione reductase, an enzyme found in trypanosomes may be used in some embodiments. Trypanothione reductase catalyzes NADPH-dependent cleavage of trypanothione, a glutathione analog used in redox regulation in trypanosomes (Mittal et al., Protein Expr. Purif., 2005 April; 40:279-86; Field et al., Mol Biochem Parasitol., 1992 January; 50:47-56; Henderson et al., Proc. Natl. Acad. Sci. USA, 1991 October; 88:8769-8773). Trypanothione reductase is active on glutathione disulfide derivatives bearing linker groups and is therefore advantageous for NADPH-catalyzed cleavage of glutathione disulfide analogs or trypanothione analogs linked to other moieties, such as ECL-active reporter molecules (i.e., ECL functional groups) or immobilization reagents (i.e., immobilizing moieties). In those embodiments using trypanothione reductase, the direct cleavage of the disulfide bond of the ECL detection reagent by NADPH-catalyzed activity of trypanothione reductase bypasses the need for glutathione and glutathione reductase as coupling reagents added to an enzyme activity reaction mixture.

When G6PD activity is present and NADPH is generated, the disulfide bond between the ECL-active ruthenium chelate and the immobilizing moiety may be broken, and the ECL-active ruthenium chelate may be washed away, resulting in a reduction of the measured ECL signal in proportion to the amount of G6PD activity present. When there is no G6PD activity, the full ECL signal will be detected, and the extent of reduction of the ECL signal toward zero can be used to quantify the activity of G6PD. A cutoff value can be established for predicting safety of administering primaquine or other drugs that cause hemolysis in people with G6PD deficiency.

In some embodiments, the assay method steps for measuring NADPH generated in a sample, may include combining a detection reagent having a disulfide bond, the sample and an NADPH-catalyzed disulfide reductase to form a reaction mixture, wherein the disulfide bond of the detection reagent is cleaved by the reductase in the presence of NADPH, wherein the detection reagent contains an ECL-active ruthenium chelate on a first side of the disulfide bond and an immobilizing moiety on a second side of the disulfide bond, wherein the cleaving yields a first cleavage product having the ECL-active ruthenium chelate and a second cleavage product having the immobilizing moiety, and wherein the cleaving by the reductase is in proportion to the amount of NADPH generated in the sample. In some embodiments, the assay method steps may also include measuring the absence, presence or amplitude of an ECL signal, wherein the absence or reduced magnitude of an ECL signal indicates the presence of NADPH in the sample, and wherein a maximal ECL signal indicates the absence of NADPH in the sample. In some embodiments, the NADPH-generating enzyme is glucose-6-phosphate dehydrogenase. In some embodiments, the disulfide-cleaving reductase is chosen from glutathione reductase and trypanothione reductase. In some embodiments, the immobilizing moiety is biotin.

In some embodiments, the assay method steps for measuring an NADPH-generating enzyme activity in a sample may include (a) combining the sample, NADP+, and a substrate specific to the enzyme to be measured within the sample, to form a reaction mixture, under conditions such that NADPH is generated, and such that the method step is allowed to react for a specified time and at a specified temperature appropriate for the particular reaction. In some embodiments, the assay method steps may also include (b) combining the reaction mixture of step (a) with glutathione reductase and glutathione disulfide under conditions that will reduce glutathione disulfide to reduced glutathione. In some embodiments, the assay method steps may also include (c) combining the reaction mixture of step (b) with a disulfide-containing detection reagent having an ECL-active ruthenium chelate on a first side of the disulfide bond, and an immobilizing moiety on a second side of the disulfide bond, wherein the disulfide-containing detection reagent is cleaved nonenzymatically by the reduced glutathione, wherein the cleaving by the reduced glutathione is in proportion to the amount of NADPH generated in the sample. In some embodiments, the assay method steps may also include (d) measuring the absence, presence or amplitude of an ECL signal, wherein the absence or reduced magnitude of an ECL signal indicates the presence of NADPH-generating enzyme in the sample, and wherein a maximal ECL signal indicates the absence of NADPH-generating enzyme in the sample. In some embodiments, step (a) is carried out over a specified time ad at a specified temperature appropriate for the particular reaction. In some embodiments, the NADPH-generating enzyme is glucose-6-phosphate dehydrogenase. In some embodiments, the disulfide-cleaving reductase is chosen from glutathione reductase and trypanothione reductase. In some embodiments, the immobilizing moiety is biotin.

In some embodiments, an electrochemiluminescent functional group, such as, an ECL-active ruthenium chelate, may be attached by intermediate linker, such as, an amino group or a carboxylate group, to one of the glutathione moieties in the GSSG. An immobilizing moiety may be linked to the other glutathione moiety in the GSSG. Suitable immobilizing moieties may include a magnetic bead linked directly or by an intermediate linker as disclosed herein, such as, biotin, which can be attached to solid phases as discussed herein, such as magnetic beads derivatized with avidin, also by either a free amino or carboxylate group. The length of the linkers to the GSSG detection reagent should be sufficient to allow glutathione reductase access to cleave the disulfide bond.

In another embodiment, GSH (reduced state of glutathione) generated by the NADPH-catalyzed action of glutathione reductase on glutathione disulfide may nonenzymatically cleave a disulfide bond of a detection reagent having an electrochemiluminescent functional group, such as, an ECL ruthenium chelate compound, and an immobilizing moiety, such as a magnetic bead or other suitable ECL assay reagent such as biotin. This eliminates the need to identify a glutathione disulfide analog capable of being cleaved by glutathione reductase or trypanothione reductase after derivatization with ECL reagents. (See, e.g., Example 1)

Similar detection reagents and ECL measurement systems may be used to link activity of other enzymes that either generate or deplete NADPH from a reaction mixture, to measure the activity of enzymes or amounts of specific substrates in a biological sample. For example, ammonia in a biological sample is measured by combining a sample with a reaction mixture comprising the enzyme glutamate dehydrogenase and its substrate alpha-ketoglutarate, which combines with ammonium and concurrently converts NADPH to NADP+. The alteration in NADPH in such a reaction mixture, permits measurement of ammonia in a sample, such as plasma or serum, using the reagents and methods disclosed herein as for detection and quantification, based on changes in an ECL signal mediated by changes in NADPH in the reaction mixture. Assays for urea or creatinine are similarly formatted using appropriate enzyme reaction mixtures known in the art that generate or deplete NADPH in proportion to the amount of urea or creatinine (or other specific metabolites of interest) present in a biological sample.

Because NADPH generation may be coupled to activities of a large variety of enzymes and to concentrations of their substrates and products, the system for measuring NADPH by ECL may be configured to detect or quantify a large variety of compounds or enzymes, including standard clinical chemistry analytes such as urea, creatinine, ammonia or other analytes known in the art to be suitable for assays involving the generation or depletion of NADPH in an assay reaction mixture.

NADH-Generating Enzymes

The detection reagents disclosed herein may also be used in assays for measuring activity of enzymes that generate or deplete NADH in a sample. Enzymes and enzyme reactions that generate NADH from NAD+ may be quantified using the detection reagents disclosed herein. For example, in some embodiments, a disulfide bond of the detection reagent may be cleaved by cystine reductase or other enzymes that produce free sulfhydryl groups in quantities proportional to the amount of NADH in a biological sample. Cystine reductase converts cysteine (the oxidized, dimeric form of the amino acid cysteine) to reduced, monomeric cysteine with a free hydroxyl group capable of cleaving the disulfide bond of the ECL detection reagent. A number of standard clinical chemistry analytes, including both enzymes and substrates (metabolites) are based on assay reaction mixtures that generate or deplete NADH, with detection by color reagents responsive to NADH or by measurement of UV absorbance changes indicating conversion of NAD+ to or from NADH. Such assays known in the art can be adapted for ECL instruments by using detection reagents and methods of the invention.

Esterases and Lipases

Other classes of enzyme activities directly form free sulfhydryl groups in proportion to the specific enzyme activity to be measured in a biological sample, including esterases and lipases acting on thioester analogs of their natural ester substrates. Thus, the detection reagents of the present disclosure may also be used in methods of measuring enzyme activity or determining the presence or absence of enzyme activity, for such enzymes as esterases and lipases. For example, the esterases chosen may use thioester analogs of natural ester or fatty acyl substrates that are specifically cleaved by the selected esterase enzyme being used. In one aspect, the substrates to the enzymes can be sn-2 thioester analogs of phosphatidyl choline, thio-PAF (platelet activating factor), or analogs thereof.

Figure 1A:
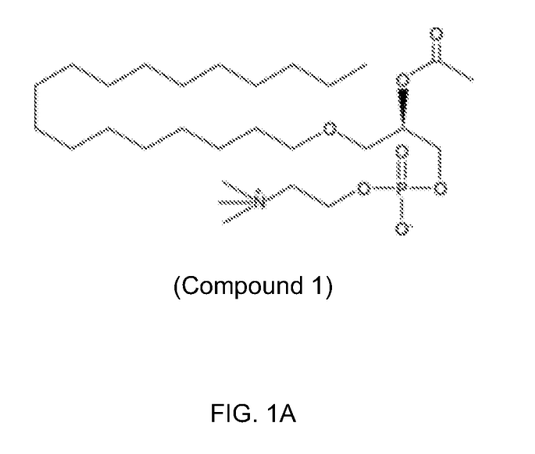
FIG. 1A is a chemical representation of the structure for platelet activating factor (PAF), labeled as Compound 1.

A natural substrate for the lipase Lp-PLA$_2$ is a phospholipid called platelet activating factor (PAF). Lp-PLA$_2$ may cleave an acetate substituent from PAF, to yield lyso-PAF. The structure for PAF is shown as Compound 1 in FIG. 1A.

Figure 1B:
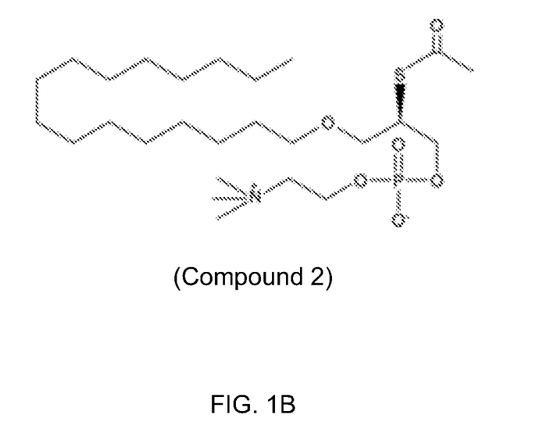
FIG. 1B is a chemical representation of the structure for thio-PAF, labeled as Compound 2.

In one aspect, thio-PAF is a suitable esterase analog for measuring activity of Lp-PLA$_2$. The deacetylating action of Lp-PLA$_2$ on this thio compound yields an analog of lyso-PAF with a free sulfhydryl group. The structure for thio-PAF is shown as Compound 2 in FIG. 1B.

Figure 1C:
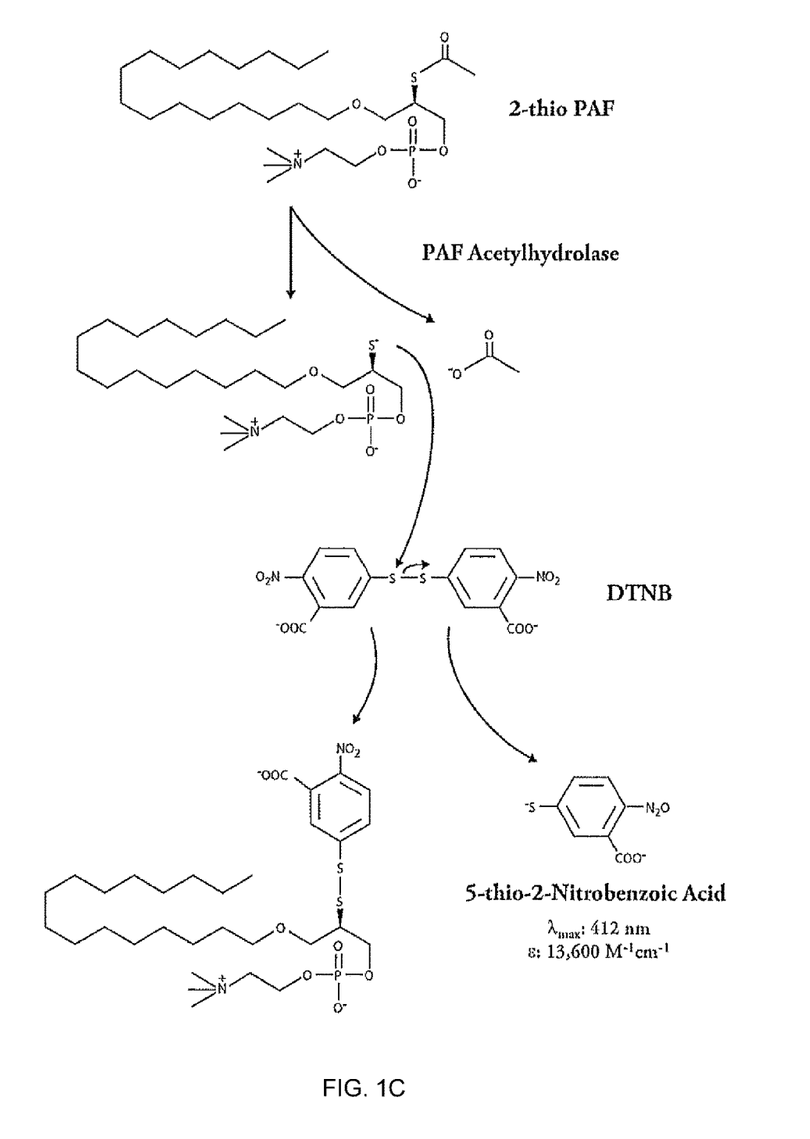
FIG. 1C is a schematic representation of the colorimetric assay using dithionitrobenzoic acid (DTNB) as a substrate.

Typically, in a colorimetric assay using this thio-PAF analog, the free sulfhydryl group is detected by cleavage of the disulfide bond in dithionitrobenzoic acid (DTNB). See, for example, FIG. 1C, which provides a schematic representation of a colormetric assay using DTNB as a substrate. A colorimetric assay may use the 2-thio-PAF, which serves as a substrate for all PAF-AHs. Upon hydrolysis of the acetyl thioester bond at the sn-2 position by PAF-AH, free thiols may be detected using 5,5'-dithio-bis-(2-nitrobenzoic acid) (DTNB). Cleavage of the disulfide bond yields 5-thio-2-nitrobenzoic acid which can be quantified with a spectrophotometer. DTNB, as a standard disulfide colorimetric reagent, also can be used in various cholinesterase assays, using thioester analogs of acetylcholine or butyrylcholine, for detection of organophosphate (cholinesterase inhibitor) poisoning, usually with some compromise due to light absorbance by hemoglobin, for example, overlapping with the detection wavelength.

Figure 1D:
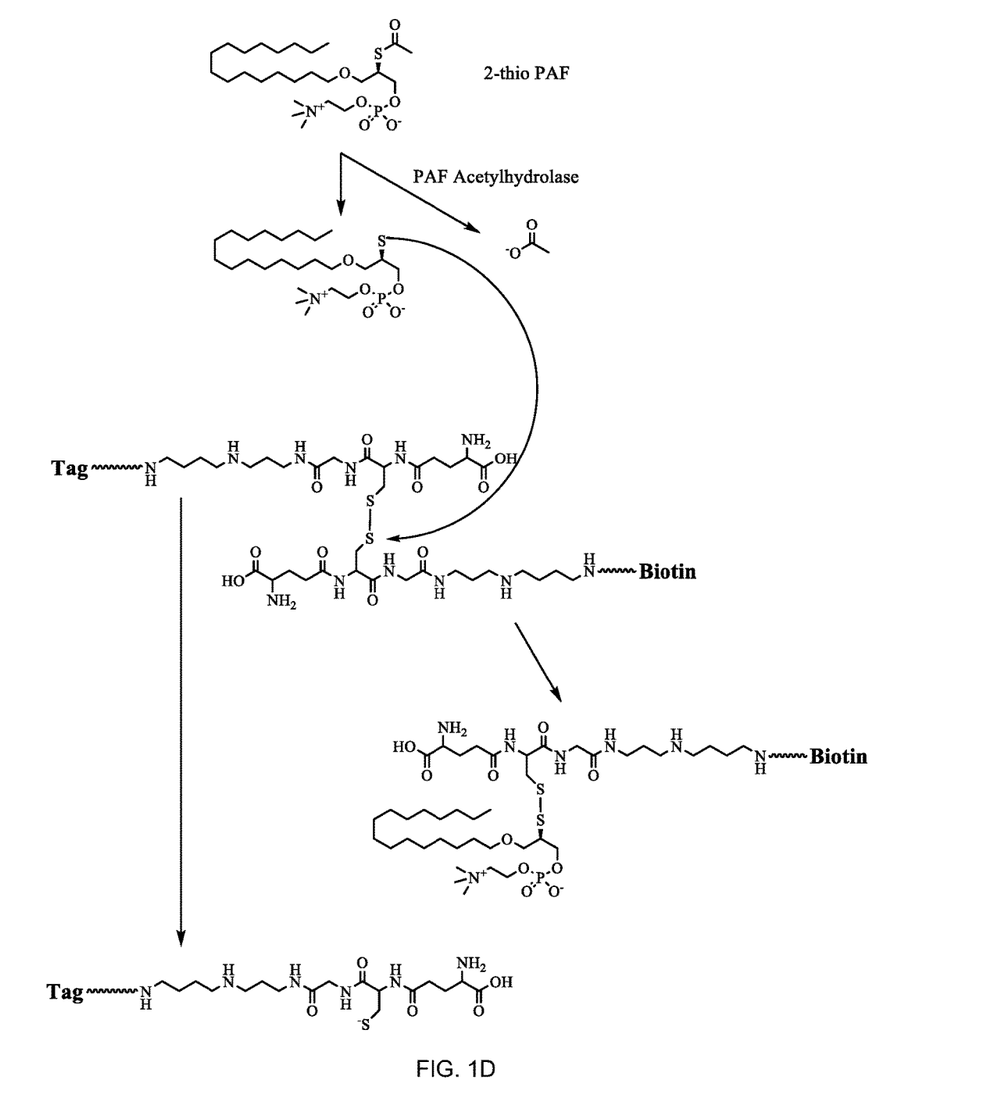
FIG. 1D is a schematic representation of an ECL assay using Glutathione Disulfide (GssG) as a detection reagent.

For adaptation to an ECL-based assay, instead of DTNB, an ECL detection reagent may be used to convert the generation of free sulfhydryl groups into a quantitative change in an ECL signal (see, e.g., FIG. 1D, a schematic representation of an ECL assay using Glutathione Disulfide (GssG) as a detection reagent). In some embodiments, for example, a suitable detection reagent may be an analog of glutathione disulfide, in which an electrochemiluminescent functional group is attached to one glutathione moiety, and an immobilizing moiety is attached to the other glutathione moiety. As discussed herein, the electrochemiluminescent functional group may be an ECL-activeruthenium (Ru) chelate, such as a ruthenium bis-pyridyl derivative. Also as discussed herein, the immobilizing moiety may be a paramagnetic bead. Intermediate linkers may be used to attach the electrochemiluminescent functional groups and the immobilizing moieties to the glutathione moieties, including those discussed herein, such as, for example, biotin attached to a streptavidin-coated paramagnetic bead. The detection reagent may generate an ECL signal when the beads are held in proximity to an ECL electrode by application of a magnet within an ECL reaction chamber, such as in a flow cell. Free sulfhydryl groups on lyso-thio-PAF may be created in proportion to the activity of Lp-PLA$_2$ in a biological sample over a specified reaction time, resulting in cleavage of the disulfide bond in the ECL detection reagent-derivatized glutathione disulfide analog, also in proportion to the activity of Lp-PLA$_2$ in the biological sample. The recorded ECL signal may therefore diminish in proportion to the amount of active Lp-PLA$_2$ in a biological sample.

In some embodiments, the assay method steps for measuring enzyme activity, such as that of esterase or lipase activity, may include combining the sample, a thioester analog of a substrate for an esterase, and a disulfide-containing detection reagent having an ECL-active ruthenium chelate on a first side of the disulfide bond and an immobilizing moiety on a second side of the disulfide bond, to form a reaction mixture, under conditions such that the thioester analog of the substrate is deacylated by esterase in the reaction mixture to yield an activated substrate analog having an exposed deacylated free sulfhydryl group which cleaves the disulfide bond of the disulfide-containing detection reagent leading to a change in a detectable ECL signal in proportion to the esterase activity in the reaction mixture. The assay method may also include the step of measuring the absence, presence or amplitude of the ECL signal, wherein the absence or reduced magnitude of the ECL signal may indicate the presence of enzyme activity in the reaction mixture, and wherein a maximal ECL signal may indicate the absence of enzyme activity in the reaction mixture.

In some embodiments, the enzyme may be an esterase. In some embodiments, the esterase may be a cholinesterase or a lipase. In some embodiments, the lipase may be Lp-PLA$_2$.

In some embodiments, examples of suitable substrates for cholinesterase may include thioester analogs of the esterase substrates acetylcholine and butyrylcholine, including, but not limited to, acetylthiocholine, propionylthiocholine or butyrylthiocholine. These substrates may be specifically cleaved by various esterases, such as cholinesterases, to expose a free sulfhydryl group that may cleave the disulfide-containing detection reagent, as compared to the thio-PAF substrate that may be more specifically cleaved by Lp-PLA$_2$.

In some embodiments, the combining step may include combining a detergent. The detergent may be a zwitterion detergent such as 3-[(3-cholamidopropyl)dimethylammonio]-1-propanesulfonate (CHAPS) or a non-ionic detergent, such as Triton™ X-100 (4-(1,1,3,3-Tetramethylbutyl) phenyl-polyethylene glycol, t-Octylphenoxypolyethoxyethanol, Polyethylene glycol tert-octylphenyl ether) by Sigma-Aldrich. In some embodiments, the method may include the step of adjusting the pH of the combined components of the combining step before the measuring step. For example, the pH may be adjusted to 5.0, 5.4, 5.6, 6.0, 6.4, 6.8, 7.0, 7.2, 7.4, 7.6, 7.8, 8.0, 8.2, 8.4 or 8.6, or pH values therebetween.

An immobilizing moiety for holding or drawing the disulfide derivatized with an ECL-active ruthenium chelate in proximity to an ECL electrode may be an ECL moiety. In some embodiments, the immobilizing moiety may be, for example, biotin.

Detection Reagent Kits

Also disclosed are kits for performing the methods described herein. For example, a kit may be used for preparing a reaction mixture that is suitable for detecting enzyme activity. Materials to be included in the kit may vary depending on the ultimate purpose. As such, the kits may include one or more components that are used in the methods. The kits disclosed herein may include at least one component selected from the following components: a detection reagent, a substrate for an enzyme, a thioester analog of a substrate for an enzyme, enzymes, glutathione disulfide, necessary buffers, standards and instructions for performing the methods disclosed herein, as well as other components and elements of the methods described herein. The standards can be additional chemical reagents or data (empirical) in printed or electronic form necessary for the calibration needed for performance of the assay.

The present disclosure can be better understood by reference to the examples included herein, which illustrate but do not limit the present teachings described herein. It is to be understood that both the descriptions disclosed herein and the following examples are merely illustrative and intended to be non-limiting.

EXAMPLES

The following examples are intended to be non-restrictive and explanatory only.

The composition of certain solutions, diluents and buffers referred to in the Examples disclosed herein may include the following:

(1) DILUENT Solution (0.024% potassium phosphate, monobasic; 0.144% sodium phosphate, dibasic; 0.7% sodium chloride, 0.02% potassium chloride; 0.33% Tween® 20; 0.104% Kathon CG-ICP II);

(2) ECL Read Solution (4.1% potassium phosphate, monobasic; 2.14% tripropylamine [TPA]; 0.88% sodium chloride; 0.02% Polidocanol [Thesit]; 0.1% Oxaban-A preservative);

(3) PBS-1 (10 mM potassium phosphate, monobasic; 140 mM potassium phosphate, dibasic (pH 7.8±0.1));

(4) Sample Buffer (100 mM Tris-HCl (pH 8.0) containing 28 mM CHAPS);

(5) Assay Buffer (100 mM Tris-HCl, pH 8.0); and (6) Bi-GssG-TAG (Biotin-glutathione disulfide-TAG Plus).

Example 1—ECL Detection and Measurement of Low mM of NADPH and G6PD 25 uL of Bi G-s-s-G TAG Plus was diluted in GR-DB to 1:300, 1 U/mL of Baker's GR and 5 mM GssG. 25 uL of NADPH was freshly prepared in GR-AB to 10 mM (9.5 mg/mL) GR-AB. The reagent was set up on a 37° C. hot plate. The preparation was mixed and shaken for 30 minutes at room temperature. 5 ug/well beads were added in 50 uL and shaken for another 10 minutes. Then the beads were washed once with 150 uL GR-AB and resuspended in 150 uL GR-AB. The following Table 1 provides the data indicating the detection of low mM of NADPH.

TABLE 1

Data Summary

| NADPH (mM/L) | ECL Signal |
|---|---|
| Buffer | 288131 |
| 0.0137 | 285630 |
| 0.0412 | 344970 |
| 0.123 | 271822 |
| 0.370 | 261365 |
| 1.11 | 149095 |
| 3.33 | 26904 |
| 10.0 | 9928 |

The following is additional data with glucose-6-phosphate dehydrogenase showing a calibrator curve illustrating that G6PD was detected. Specifically, the data with blood lysate showed a decrease of signal with 100% blood lysate.

The method was as follows. To 50 uL of G6PD substrate mixture Glutathione Reductase Assay Buffer (containing Bi G-s-s-TAG Plus (substrate), NADP+ at 10 mM, G6P at 30 mM, Glutathione Reductase 2 U/mL, GssG 30 mM, Mg++ 10 mM) was added 25 uL of G6PD (point dilution from 2.0 U/mL). The mixture was shaken for 30 minutes at room temperature. 25 uL of beads were added to each well (400 ug/mL) and shaken for an additional 10 minutes. The beads were washed once and finally in 150 uL of GR-AB. Tables 2A and 2B below provide the results.

TABLE 2A

Data Summary

| Purified G6PD (U/mL) | Signal | Mean Signal | % CV |
|---|---|---|---|
| 0 | 624347 575980 | 600164 | 5.7% |
| 0.200 | 504924 531403 | 518164 | 3.6% |
| 0.40 | 384476 398040 | 391258 | 2.5% |
| 0.60 | 296456 285718 | 291087 | 2.6% |
| 0.80 | 267842 257318 | 262580 | 2.8% |
| 1.00 | 189270 207632 | 198451 | 6.5% |
| 1.50 | 116890 126295 | 121593 | 5.5% |
| 2.00 | 85606 94262 | 89934 | 6.8% |

TABLE 2B

Data Summary

| Blood Lyate | Signal | Mean Signal | % CV |
|---|---|---|---|
| 0% | 583817 619656 | 601737 | 4.2% |
| 25% | 618866 628400 | 623633 | 1.1% |
| 50% | 593338 557307 | 575323 | 4.4% |
| 100% | 394744 491048 | 442896 | 15.4% |

Example 2—Preparation of Four Different Homo- and Mixed-Oxidized Glutathione/glutathionylspermaidine Substrates The following is a summary of results illustrating that the glutathione reductase failed to break the disulfide bond in glutathinone, glutathionylspermidine or mixed thione substrates after being modified with biotin and TAG Plus. The following homo- and mixed-oxidized glutathione/glutathionylspermidine substrates were prepared: (1) Bi G-s-s-G TAG Plus; (2) Bi Gspd-s-s-Gspd TAG Plus; (3) Bi G-s-s-Gspd TAG Plus; (4) Bi Gspd-s-s-G TAG Plus.

The disulfide lineages of biotin and TAG Plus in all 4 substrates above were confirmed and verified with DTT reduction experiments and DTT was able to knock off 40%→90% of TAG Plus. However, the glutathione reductase from Baker's Yeast and from human failed to cleaved any one of the 4 substrates. The digestions were all done in the fluid phase. Substrates were first incubated with enzyme with NADPH and then incubated with beads making sure that there was not steric hindrance issue of the substrate and beads. Bi G-s-s-G was susceptible to cleavage by reduced glutathione (GSH) generated from G-s-s-G by glutathione reductase in the presence of NADPH, permitting quantification of NADPH, whether added to the assay sample or formed as a result of G6PD activity.

Example 3—Testing ECL Assay for Activity of Lp-PLA$_2$

This experiment was performed to test the ability of an ECL detection reagent that is suitable to convert the generation of free sulfhydryl groups into a quantitative change in an ECL signal. The ECL detection reagent is an analog of glutathione disulfide, in which one glutathione moiety is derivatized with a ruthenium chelate such as a ruthenium bis-pyridyl derivative. The other glutathione moiety is immobilized onto a paramagnetic bead by attaching biotin to this second glutathione group and mixing it with a streptavidin-coated paramagnetic bead.

The assay was prepared according to the steps that follow. The Bi-GssG-TAG was prepared at a concentration of 81.6 nmol contained 18 nmol biotin and 150 nmol TAG Plus in PBS-1 buffer. The substrate (2-thio-PAF) was prepared at 200 µM with 54 pmol Bi-GssG-TAG ECL reagent in assay buffer (0.1M Tris-HCl, pH 7.2). A calibrator curve was formulated with rhLp-PLA2 in assay buffer (0.1M Tris-HCl, pH 7.2) at concentrations of 0, 62.5, 125, 500, 1000 ng/mL. The assay was run on an electrochemiluminescent (ECL) based detection analyzer (Wellstat M1M, Cat#310806) modified for sample volume by shortening tubing lengths where applicable and reducing the flow cell inlet hole diameters and measurement area and volume. The software used on the analyzer is a research version of the software that allows for adjustable parameters. The sequence of operation parameters were also modified for sample volume in this research software. An instrument with these modifications was designated MeM1. The results are summarized in Table 3 below.

TABLE 3

Data Summary

| Sample | Mean ECL | % GssG Cleavage |
|---|---|---|
| 1000 ng/mL | 84396 | −1.6 |
| 500 ng/mL | 81950 | 1.4 |
| 125 ng/mL | 83865 | −0.9 |
| 62.5 ng/mL | 82202 | 1.1 |
| No Enzyme Control | 83091 | 100 |

Example 4—Effect of pH on Disulfide Reduction of Bi-GssG-TAG

It was generally contemplated that the lyso-PAF is slow in reducing disulfides at low pH. Thiolates, not thiols, attack disulfide bonds. Hence, thiol-disulfide exchange is inhibited at low pH (typically, below 8) where the protonated thiol form is favored relative to the deprotonated thiolate form. The assay was performed essentially as described in Example 3 with pH of assay buffer increased to pH 8.0 and pH 8.3 from pH 7.2. The data is summarized in Table 4.

TABLE 4

Data Summary

| | pH 8.0 | | pH 8.3 | |
|---|---|---|---|---|
| Sample | ECL | % GssG Cleavage | ECL | % GssG Cleavage |
| 500 ng/mL | 141828 | −0.6 | 142774 | 3.4 |
| No Enzyme Control | 140984 | 100 | 147863 | 100 |

Example 5—Effect of Surfactants on Surface Tension of Protein at pH 8.0

A possible complication of working with esterases is that thio-PAF could form micelles. Formation of micelles could then restrict access (or reduce the rate of interactions) of the sulfhydryl group to hydrophilic, slightly bulky GssG or especially Bi-GssG-TAG. This effect might then be minimized by the addition of surfactant reagents. Therefore, the ability of Triton™ X-100, CHAPS, and Digitonin to reduce the formation of micelles was studied. Therefore, in this experiment the three compounds listed in Table 5 were tested for their ability to reduce micelle formation in Lp-PLA$_2$ activity assay.

TABLE 5

Surfactants

| Reagents | Manufacturer | Catalog Number |
|---|---|---|
| Digitonin | Sigma | D-5628 |
| CHAPS | Sigma | C-9426 |
| Triton ™ X-100 | Sigma | T-9284 |

Digitonin, CHAPS or Triton™ X-100 were added to the enzyme to give a final concentration of 0.05%, 7 mM and 8 mM, respectively. The rhLp-PLA2 sample (500 ng) in respective detergents maintained at room temperature 25±2° C., was added to assay wells (in duplicate) followed by 50 µL of substrate containing Bi-GssG-TAG and 25 µL of washed M270-SA (Streptavidin) beads (Life Technologies Catalog#65305). The assay plate was placed on a Micromix plate shaker (Seimens/DPC) set at Form 8 & Amp 6, covered with a plate cover and incubated for 10±1 minutes at room temperature. The assay plate was washed once with 150 µL/well of DILUENT solution. The magnetic bead complexes were pelleted by placing the assay plate on a LifeSep 96F plate magnet (Dexter Magnetic Technologies) for 2±0.5 minutes. The assay well solution volumes were decanted and any residual liquid was removed by quickly inverting the plate and pat it against a stack of paper towels. The pelleted magnetic bead complexes were resuspended, washed by adding 150 µL of ECL Read Solution to each well and agitating the plate on the Micromix plate shaker for 2±0.5 minutes (at Form 8 & Amp 6) and decanted as described above. After the wash the magnetic bead complexes were re-suspended with 150 µL/well of DILUENT Solution and agitated as described above for 2±0.5 minutes. The assay plate was evaluated on one MeM1 analyzer using the single buffer system (ECL Read Solution) and Wasabi version 2.02.0039. The results are summarized in Table 6 below.

TABLE 6

Data Summary

| Sample | Mean ECL | % GssG Cleavage* |
|---|---|---|
| Enz + 7 mM CHAPS | 532128 | 12 |
| Enz + 0.05% Digitonin | 641843 | −6.7 |
| Enz + 8 mM Triton ™ X-100 | 543511 | 10 |
| Enz w/o detergent | 602280 | 0.0 |
| No Enz control | 601731 | 0.0 |

*% Differences in disulfide cleavage when compared to the untreated sample

The results indicated CHAPS and Triton™ X-100 effectively reduced the formation of micelles, this made the substrate lyso-thio-PAF more accessible for the thio group to be exchanged and led to a reduction of the ECL signal when compared to the control sample (enzyme without detergent treatment). Digitonin showed no affect in reducing micelles formation possibly due to the ethanol contained in the solution (digitonin is soluble in ethanol only).

Example 6—Concentration Dependent Effect of CHAPS and Triton™ X-100 at pH 8.0 on the ECL Signal in an Lp-PLA$_2$ Assay The concentration dependent effect of CHAPS and Triton™ X-100 on the improvement of disulfide detector reagent in the Lp-PLA$_2$ activity assay was studied using 7 mM, 10 mM and 20 mM CHAPS and 8 mM, 15 mM and 30 mM Triton™ X-100 with 500 ng of rhLp-PLA$_2$ enzyme. CHAPS and Triton™ X-100 were dissolved in DI water, and added to sample buffer at the appropriate concentrations. The substrate and Bi-GssG-TAG were also diluted in sample buffer at the appropriate concentration. The assay was performed with the combination of 50 μL volumes of enzyme sample, 50 μL of substrate containing Bi-GssG-TAG and 25 μL of M270-SA beads as described in Example 5 and results summarized in Table 7 below.

TABLE 7

Concentration Dependent Effect of CHAPS and Triton™ X-100 at pH 8.0

| Sample | Mean ECL | % GssG Cleavage |
| --- | --- | --- |
| Enz + 7 mM CHAPS | 719992 | 2.7 |
| Enz + 10 mM CHAPS | 664725 | 10 |
| Enz + 20 mM CHAPS | 622456 | 16 |
| Enz + 8 mM Triton™ X-100 | 631116 | 15 |
| Enz + 15 mM Triton™ X-100 | 639357 | 14 |
| Enz + 30 mM Triton™ X-100 | 624795 | 16 |
| Enzyme w/o Detergent | 713972 | 0.0 |
| No Enzyme Control | 739614 | 0.0 |

The results indicated that CHAPS provided a concentration dependent increase in GssG cleavage by the lipase reaction product, with the greatest effect occurring with 20 mM of CHAPS (Table 7). The addition of Triton™ X-100 also led to disulfide reduction.

Example 7—Disulfide Reduction Using Sample Buffer Containing 28 mM CHAPS at pH 8.0

The ability of sample buffer containing 0.1 M Tris-HCL, pH 8.0 and 28 mM CHAPS to reduce the disulfide bond in the Lp-PLA$_2$ activity assay was examined in duplicate experiments by spiking Lp-PLA$_2$ enzyme at 2000 ng/mL, 800 ng/mL, 80 ng/mL, 8.0 ng/mL and 0 ng/mL into sample buffer, using the assay format described in Example 5 modified to employ an 5-point calibrator curve.

Figure 2:
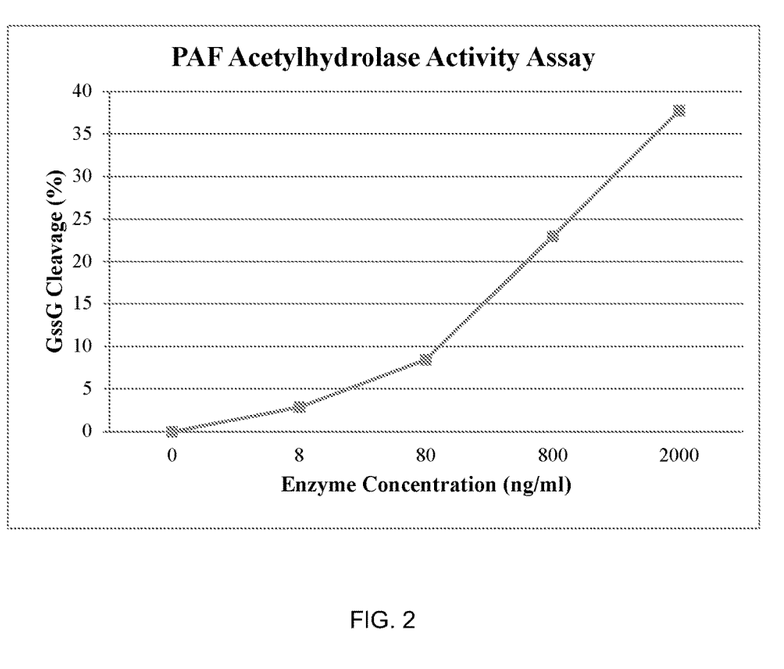
FIG. 2 is a graphical representation of the data collected from a disulfide reaction described in Example 7 showing GssG Cleavage (%) vs. Enzyme Concentration (ng/mL).

A Bi-GssG-TAG was prepared at a concentration of 81.6 nmol and contained 18 nmol biotin and 150 nmol TAG Plus (ruthenium bis-pyridyl derivative). 1:1500 dilution of the reagent was used in reaction. A calibrator curve was formulated with rhLp-PLA$_2$ enzyme in sample buffer at concentrations of 0.0, 8.0, 80, 800 and 2000 ng/mL. A substrate (2-thio-PAF) was prepared at 200 μM in assay buffer with 54 pmol Bi-GssG-TAG reagent. Dynabeads M270-SA were washed and resuspended at 0.1 mg/mL in assay buffer. The assay was performed essentially as described in Example 6. The results are summarized in Table 8 and illustrated in graphical representation of the data in FIG. 2.

TABLE 8

Data Summary from Disulfide Reduction using Sample Buffer Containing 28 mM CHAPS at pH 8.0

| Enz. Conc. (ng/ml) | ECL | % GssG Cleavage |
| --- | --- | --- |
| 0 | 147275 | 0.0 |
| 8 | 143034 | 2.9 |
| 80 | 134823 | 8.5 |
| 800 | 113400 | 23 |
| 2000 | 91636 | 38 |

Results from the experiment indicated that in the presence of CHAPS at 28 mM in the sample buffer increased the cleavage of disulfide bond in Lp-PLA$_2$ by an average of 2.9%, 8.5%, 23%, and 38% for Lp-PLA$_2$ enzyme spikes of 8.0 ng, 80 ng, 800 ng and 2000 ng/mL respectively (Table 8). Results also demonstrate the principle in which the Biotin-glutathione disulfide-TAG substrate can convert the generation of free sulfhydryl groups into a quantitative change in an ECL signal.

While various embodiments have been described, it is to be understood that variations and modifications may be resorted to as will be apparent to those skilled in the art. Such variations and modifications are to be considered within the purview and scope of the claims appended hereto.

The present disclosure includes a number of other example features such as those explained hereinafter. It is to be understood that both the descriptions disclosed herein are examples only. The examples are merely illustrative and intended to be non-limiting. Moreover, it should be understood that various features and/or characteristics of differing embodiments herein may be combined with one another. It is therefore to be understood that numerous modifications may be made to the illustrative embodiments and that other arrangements may be devised without departing from the scope of the present disclosure. Other embodiments will be apparent to those skilled in the art from consideration of the disclosure and practice of the various example embodiments disclosed herein. It is intended that the specification and examples be considered as examples only, with the true scope of the invention being indicated by the claims.

It is also to be understood that, as used herein the terms "the," "a," or "an," mean "at least one," and should not be limited to "only one" unless explicitly indicated to the contrary. Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points within the example ranges and values provided. Efforts have been made to ensure the accuracy of the numerical values disclosed herein. Any measured numerical value, however, can inherently contain certain errors resulting from the standard deviation found in its respective measuring technique.

All publications, patents and patent applications mentioned in this specification are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online.

The invention claimed is:

1. A detection reagent, comprising:
a molecule having a cleavable disulfide bond with an electrochemiluminescence (ECL)-active ruthenium chelate on a first side of the disulfide bond and an immobilizing moiety on a second side of the disulfide bond, wherein the disulfide bond of the detection reagent is capable of being cleaved by a free sulfhydryl group, and
wherein the free sulfhydryl group is exposed by one or more components in a reaction mixture,
the molecule which is measurable within the reaction mixture by the absence, presence or amplitude of an ECL signal, wherein the cleaving by the free sulfhydryl group is in proportion to the amount of enzyme generated in the sample.

2. A method of preparing the detection reagent of claim 1, comprising:
attaching to a molecule having a disulfide bond, an electrochemiluminescence (ECL)-active ruthenium chelate on a first side of the disulfide bond and an immobilizing moiety on a second side of the disulfide bond.

3. The method of claim 2, wherein the disulfide bond of the detection reagent is capable of being cleaved by a free sulfhydryl group.

4. A method of preparing the detection reagent of claim 1, comprising:
attaching an electrochemiluminescent functional group to a first molecule having a sulfide group capable of forming a disulfide bond;
attaching an immobilizing moiety to a second molecule having a sulfide group capable of forming a disulfide bond; and
forming a cleavable disulfide bond between the first molecule and the second molecule.

5. The method of claim 4, wherein the disulfide bond of the detection reagent is capable of being cleaved by a free sulfhydryl group.

6. A method of preparing the detection reagent of claim 1, comprising:
forming a cleavable disulfide bond between a first molecule and a second molecule;
attaching an electrochemiluminescent functional group to the first molecule; and
attaching an immobilizing moiety to the second molecule.

7. The method of claim 6, wherein the disulfide bond of the detection reagent is capable of being cleaved by a free sulfhydryl group.

8. A method for measuring NADPH generated in a sample, comprising:
combining the detection reagent of claim 1 having a disulfide bond, the sample and an NADPH-catalyzed disulfide reductase to form a reaction mixture, wherein the disulfide bond of the detection reagent is cleaved by the reductase in the presence of NADPH,
wherein the cleaving yields a first cleavage product having the ECL-active ruthenium chelate and a second cleavage product having the immobilizing moiety, and
wherein the cleaving by the reductase is in proportion to the amount of NADPH generated in the sample; and
measuring the absence, presence or amplitude of an ECL signal, wherein the absence or reduced magnitude of an ECL signal indicates the presence of NADPH in the sample, and wherein a maximal ECL signal indicates the absence of NADPH in the sample.

9. The method of claim 8, wherein the NADPH is generated by glucose-6-phosphate dehydrogenase.

10. The method of claim 8, wherein the disulfide-cleaving reductase is chosen from glutathione reductase and trypanothione reductase.

11. The methods of claim 8, wherein the immobilizing moiety is biotin.

12. A method for measuring NADPH-generating enzyme activity in a sample, comprising:
(a) combining the sample, NADP+, and a substrate specific to the enzyme to be measured within the sample, to form a reaction mixture under conditions such that NADPH is generated from reduced NADP+;
(b) combining the reaction mixture of step (a) with glutathione reductase and glutathione disulfide under conditions that will reduce glutathione disulfide to GSH;
(c) combining the reaction mixture of step (b) with the detection reagent of claim 1, wherein the disulfide bond of the detection reagent is cleaved nonenzymatically by the reduced glutathione,
wherein the cleaving by the reduced glutathione is in proportion to the amount of NADPH generated in the sample; and
(d) measuring the absence, presence or amplitude of an ECL signal, wherein the absence or reduced magnitude of an ECL signal indicates the presence of NADPH-generating enzyme in the sample, and wherein a maximal ECL signal indicates the absence of NADPH-generating enzyme in the sample.

13. The method of claim 12, wherein step (a) is carried out over a specified time and at a specified temperature.

14. The method of claim 12, wherein the NADPH-generating enzyme is glucose-6-phosphate dehydrogenase.

15. The methods of claim 12, wherein the immobilizing moiety is biotin.

16. A method for measuring esterase activity in a sample, comprising:
combining the sample, a thioester analog of a substrate for an esterase, and the detection reagent of claim 1, to form a reaction mixture, under conditions such that the thioester analog of the substrate is deacylated by esterase in the reaction mixture to yield an activated substrate analog having an exposed deacylated free sulfhydryl group which cleaves the disulfide bond of the detection reagent leading to a change in a detectable ECL signal in proportion to the esterase activity in the reaction mixture; and
measuring the absence, presence or amplitude of an ECL signal, wherein the absence or reduced magnitude of an ECL signal indicates the presence of esterase in the sample, and wherein a maximal ECL signal indicates the absence of esterase in the sample.

17. The method of claim 16, wherein the esterase is Lp-PLA$_2$ (platelet activating factor acetylhydrolase).

18. The method of claim 16, wherein the thioester analog of a substrate is chosen from thio-platelet activating factor (PAF), lyso-thio-PAF, acetylthiocholine, propionylthiocholine and butyrylthiocholine.

19. The method of claim 16, wherein the immobilizing moiety is biotin.

20. The method of claim 16, the combining step further comprising combining a detergent.

21. The method of claim 20, wherein the detergent is chosen from CHAPS (cholamidopropyl)dimethylammonio]-1-propanesulfonate) and Triton™ X-100 (4-(1,1,3,3-Tetramethylbutyl)phenyl-polyethylene glycol, t-Octylphenoxypolyethoxyethanol, Polyethylene glycol tert-octylphenyl ether).

22. The method of claim 16, further comprising the step of adjusting the pH after the combining step and before the measuring step.

23. A kit for measuring esterase activity in a sample, comprising:
the detection reagent of claim 1;
a thioester analog of a substrate for an esterase; and
instructions for performing an esterase activity measuring assay including the steps of combining the sample, a thioester analog of a substrate for an esterase, and the detection reagent, to form a reaction mixture, under conditions such that the thioester analog of the substrate is deacylated by esterase in the reaction mixture to yield an activated substrate analog having an exposed deacylated free sulfhydryl group which cleaves the disulfide bond of the detection reagent leading to a change in a detectable ECL signal in proportion to the esterase activity in the reaction mixture; and measuring the absence, presence or amplitude of an ECL signal, wherein the absence or reduced magnitude of an ECL signal indicates the presence of esterase in the sample, and wherein a maximal ECL signal indicates the absence of esterase in the sample.

24. The kit of claim 23, wherein the esterase activity measuring assay measures the activity of an esterase selected from the group consisting of a lipase and a cholinesterase.

25. The kit of claim 23, wherein the esterase is a lipase.

26. The kit of claim 23, wherein the lipase is Lp-PLA$_2$ (platelet activating factor acetylhydrolase).

* * * * *